United States Patent [19]

Branecky et al.

[11] 4,198,351

[45] Apr. 15, 1980

[54] FORMALDEHYDE PRODUCTION PROCESS

[75] Inventors: Anthony J. Branecky, Kingsville; David W. Harris, Corpus Christi, both of Tex.

[73] Assignee: Celanese Corporation, New York, N.Y.

[21] Appl. No.: 787,739

[22] Filed: Apr. 15, 1977

[51] Int. Cl.² ............................................. C07C 45/16
[52] U.S. Cl. .................................. 260/603 C; 260/606
[58] Field of Search .................... 260/603, 603 C, 606

[56] References Cited

U.S. PATENT DOCUMENTS

| | | | |
|---|---|---|---|
| 2,643,269 | 6/1953 | Augustine | 260/603 C |
| 3,928,461 | 12/1975 | Diem | 260/603 C |
| 3,996,259 | 12/1976 | Lee | 260/465 B |
| 4,010,208 | 3/1977 | Aicher et al. | 260/603 C |

*Primary Examiner*—Warren B. Lone
*Attorney, Agent, or Firm*—Stewart N. Rice; Ralph M. Pritchett

[57] ABSTRACT

An improvement in the process for production of formaldehyde wherein a vapor phase mixture of methanol and air are passed over a silver catalyst, comprising the incorporation of a small amount of a halogen-containing compound into the mixture.

20 Claims, No Drawings

FORMALDEHYDE PRODUCTION PROCESS

BACKGROUND OF THE INVENTION

A well-known and widely used process for producing formaldehyde involves the passing of a mixture of methanol and air over or across a silver catalyst. Such process combines dehydrogenation and oxidation to obtain the formaldehyde, and such is well described in the literature.

In conducting the reaction the methanol-air mixture is contacted with a silver catalyst at elevated temperatures. In most processes, the silver is present as silver crystals in a bed which is on the order of 1 to 4 centimeters thick and through which the air-methanol mixture is passed. The silver crystals generally form a sintered cake after a period of time. It is known, however, to employ the silver catalyst in other forms, such as in the form of a fluidized bed, or on a catalyst support such as silica gel. Use of a bed of silver crystals is preferred. Contact times for the air-methanol mixture with the silver catalyst may vary widely, but will generally be on the order of 0.005 to 0.05 seconds, preferably from 0.007 to 0.03 seconds.

The molar ratio of air to methanol in the mixture contacted with the catalyst should be at least 0.8 moles of air per mole of methanol and is more usually within the range of 0.9 to 1.4 moles of air per mole of methanol. The mixture which is passed over the catalyst is not limited to methanol and air since various diluents have been disclosed in the literature as being suitably present. Also, recycled formaldehyde may be present. Included among diluents which may be present are steam, carbon dioxide, nitrogen and the like. Where very high air to methanol ratios are utilized, the use of a diluent may especially be desired in order to avoid flammable mixtures.

The pressure utilized in conducting the reaction is usually within the range of one to three atmospheres absolute, although higher or lower pressures may be utilized if desired. Relatively high temperatures are involved since the reaction is exothermic overall even though both an indothermic and exothermic reaction are involved. Since the reaction is exothermic overall no heat addition to the reaction zone is necessary. The methanol does, however, have to be preheated to a temperature at least sufficient to vaporize such, and, preferably both the air and the methanol, and any diluents, are preheated to some degree. Generally the air and any diluent will be preheated separately and apart from the methanol. The methanol-air feed mixture passed to and contacted with the silver catalyst is generally at a temperature within the range of about 70° C. to 125° C., preferably 75° C. to 100° C.

Due to the fact that the reaction is overall exothermic in nature, the temperature of the catalyst bed will generally be within the range of 475° C. to 675° C., and preferably such is within the range of 550° C. to 625° C. The temperature of the catalyst bed can be regulated by controlling preheat temperature of the feed, and by controlling the ratio of air to methanol.

The foregoing background discussion is very general in nature and those skilled in the art are aware of numerous literature references to variations on the basic process. Despite the fact that the silver catalyst method has been thoroughly researched and in commercial use for years, improvements in the process are still being sought. It is thus an object of the present invention to provide an improvement in the process for the production of formaldehyde by the silver catalyzed reaction of methanol and air. It is a particular object of the present invention to provide an improvement in such process whereby a greater selectivity to formaldehyde may be attained. Additional objects will become apparent from the following description of the invention.

SUMMARY

The foregoing and additional objectives are accomplished by the present invention which in one of its aspects is an improvement in a vapor phase process for the production of formaldehyde wherein a vapor phase mixture comprising methanol and air are contacted with a silver catalyst to produce a formaldehyde-containing product, which improvement comprises incorporating a small amount of a halogen-containing compound, in the vapor phase, into the mixture comprising methanol and air which is contacted with the said silver catalyst, the amount of which halogen-containing compound being an amount which will increase the selectivity of the reaction to formaldehyde but which will not cause loss of reaction.

The terms "conversion" and "selectivity" as used in the specification and in the claims are defined as follows:

$$\text{Conversion, mole \%} = \frac{\text{moles methanol converted}}{\text{moles methanol fed}} \times 100$$

$$\text{Selectivity, mole \%} = \frac{\text{moles of formaldehyde produced}}{\text{moles methanol converted}} \times 100$$

The use of a halogen-containing compound to modify the silver catalyzed reaction of ethylene with oxygen to produce ethylene oxide is disclosed in the prior art; for example, see U.S. Pat. No. 3,119,837 issued Jan. 28, 1964 to H. A. Kingsley, et al. In view of the unpredictability of catalysts, the beneficial results obtained by use of a halide in the silver catalyzed production of formaldehyde was entirely unexpected and unpredictable.

DETAILED DESCRIPTION OF THE INVENTION

The present invention resides in the discovery that incorporation of a small amount of a halogen-containing compound (hereafter sometimes referred to as a "halide") into the methanol-air mixture will increase the selectivity to formaldehyde. By "halide" is meant an organic compound having one or more halogen atoms as substituents thereon. By the word "halogen" is meant the elements fluorine, chlorine, bromine and iodine. The halide must be one which will exist as a vapor under the reaction conditions and should be substantially inert; that is, the halide should not react to any appreciable extent under reaction conditions with itself or with the other components in the feed mixture or the reaction effluent. Best results will be obtained with boron trifluoride or with organic halides.

Preferred organic halides are those which are halocarbons or halohydrocarbons, more especially those having a boiling point at atmospheric pressure of less than about 100° C. Especially preferred organic halides are the acyclic halocarbons and halohydrocarbons, particularly those of 1 to 5 carbon atoms. By the term "halocarbon" is meant a compound composed only of carbon and halogen atoms, and, by the term "halohydrocarbon" is meant a compound composed only of carbon, hydrogen and halogen atoms. The organic halide may be saturated or unsaturated, with saturated halides being preferred. By the term "saturated" is meant free of ethylenic and acetylenic unsaturation. The organic halide can have one or more halogen atoms as substituents thereon, and, can have more than one kind of halogen substituent, although it is preferred that only a single type of halogen be present. Specific organic halides which are useful in the present invention are dichloromethane, carbon tetrachloride, tetrafluoromethane, chloroform, methyl bromide, bromotrichloromethane, bischloromethyl ether, dibromoethane, difluoromethane, 1,2-dichloroethane, hexafluoroethane, ethyl bromide, ethyl iodide, 1,1,1,2-tetrabromo ethane, trichloro-trifluoroethane, octafluoropropane, 2-chlorobutane, 2-iodobutane, 3-chloropentane, and 1-iodopentane.

Except for halides which are gases at room temperature, the preferred method for incorporating the organic halide into the methanol-air mixture is to mix the organic halide with the methanol prior to vaporization thereof. For those halides which are gases at room temperature, such as many of the fluorocarbons, the halide may conveniently be added to the vaporized methanol, preferably as a dilute solution of the halide in nitrogen. Other methods of incorporating the halide into the feed mixture will be obvious, the only requirement being that the halide be a part of the mixture of reactants, and any diluents, etc., which is contacted with the silver catalyst. For example, an organic halide may even be formed in situ if desired as by addition of a haloacid, such as hydrochloric acid, which will react with the methanol and any recycled formaldehyde which may be present to form organic halides. Although some improvement has been obtained by this method, it si preferred to have the organic halide itself and not form such in situ by use of an acid.

The amount of halide utilized in the present invention is very small. Depending on the particular halogen, the amount provided will generally be at least 1 p.p.m. (parts per million) by weight of halogen based on the weight of methanol in the mixture. Unless specifically set forth, all references hereinafter made in this specification and in the claims to p.p.m. halogen are on the foregoing basis, that is, p.p.m. halogen by weight based on the weight of methanol. Further, such references to the amount of halogen in the mixture includes the total amount of halogen atoms present in the halide incorporated into the mixture, and is not meant to imply that such amount of halogen is present in the form of molecular halogen, atomic halogen or ionic halogen. It is not known what actually happens to the halide at the time it is being contacted with the silver catalyst although some of the organic halides decompose during passage through the reaction zone. In any event, the halogen amount specified herein and in the claims takes into account the entire amount of halogen atoms which are substituents of the halide incorporated into the mixture.

Only enough of the organic halide need be added to effect an increase in the selectivity of the reaction to formaldehyde. The required amount of halide will vary widely depending on the particular halogen being utilized. The addition of too much of some of the halogens will cause detrimental effects and a loss of reaction. For a halide where chlorine is the only halogen substituent, the chlorine concentration should be less than about 100 p.p.m., for example, generally within the range of about 10 to 95 p.p.m., and preferably within the range of about 45 to 85 p.p.m. Above about 100 p.p.m. chlorine a loss of reaction occurs. When utilizing a bromide, the bromine concentration should be less than about 70 p.p.m., for example, generally within the range of about 5 to 60 p.p.m., and preferably within the range of about 10 to 40 p.p.m. Above about 70 p.p.m. bromine, a loss of reaction occurs.

When utilizing an iodide, the iodine concentration should be less than about 7 p.p.m., for example, generally within the range of about 0.5 to 6 p.p.m., and preferably within the range of about 2 to 5 p.p.m. Above about 7 p.p.m. iodine, a loss of reaction occurs.

For fluorides, relatively large amounts are required and no loss of reaction has been observed when using fluorine compounds although there may be an amount which will cause loss of reaction. Generally, the amount of fluorine should be within the range of about 200 to 600 p.p.m., preferably within the range of 350 to 500 p.p.m.

Other factors than the amount of halide required may also affect the choice of which type of halogen compound is to be utilized. For example, organic chlorides seem to undergo decomposition across the reaction zone and can impose corrosion problems. In this respect the fluorine compounds were found to be most stable. It has also been observed that organic iodides can lead to a slight oxygen passage through the catalyst bed. In view of all the factors involved, organic bromides are the preferred halides for use in the present invention.

Conventional methods may be utilized to recover the formaldehyde product from the reaction zone effluent. Generally such involves the rapid cooling, with water quench if desired, of the effluent so as to cause condensation of components such as formaldehyde, water, and unreacted methanol. The condensed liquid may then be further treated by absorption, distillation and the like to recover the product. Most commercial processes include the recycling of a stream from the recovery section containing formaldehyde and unreacted methanol to the methanol vaporizer.

The surprising degree to which the use of a halide increases the selectivity of the process is illustrated by the following examples.

EXAMPLES

A laboratory micro unit was assembled for the oxidation of methanol to formaldehyde over a silver catalyst. The apparatus consisted of, in series, a methanol feed tank, a methanol vaporizer, a reactor, and a recovery system. A valve was located in the conduit leading from the methanol vaporizer to the reactor inlet whereby air could be introduced to the system and mixed with vaporized methanol to form a methanol-air feed mixture which was passed to the reactor. The reactor consisted of a monel tube having an inside diameter of 22 millimeters and a length of 25.4 centimeters. Located within the reactor, near the exit end thereof, was a bed of silver crystals, such bed being 25.4 millimeters in depth suspended on a copper grate through which the methanol-air mixture passed.

The effluent from the reactor was immediately passed through a condenser in order to cool such. After being cooled, the reactor effluent was passed to the base of a water absorber tower, a crude aqueous solution of formaldehyde product being removed from the base of the absorber. Removed overhead from the absorber was vent gas comprised mainly of hydrogen, nitrogen, methylformate, carbon monoxide, carbon dioxide, and oxygen. Several Runs were made in the apparatus described above, wherein about 11,200 cubic centimeters per minute (as measured at 20° C. and atmospheric pressure) of vaporized methanol was mixed with about 12,310 cubic centimeters per minute (as measured at 20° C. and atmospheric pressure) of air and the resulting mixture passed to the reactor. In all of the Runs the air-to-methanol molar ratio was 1.10:1. The initial portion of each Run was conducted in the absence of an added halogen compound with the various system parameters, conversion and selectivity determined; and, then, a halogen compound was added to the feed and the various system parameters, conversion and selectivity again determined after sufficient time to allow stabilization. Except for the octafluoropropane, which was added directly to the vaporized methanol as a gas, all the halogen compounds were added to the methanol before preheating it. The boron trifluoride was added to the methanol in the form of a 37% solution in butyl ether. The results and various parameters of the several Runs are shown in the following Table I. The pressures shown in Table I are atmospheres absolute; and, the p.p.m. halogen shown in Table I are parts per million by weight of halogen based on the weight of methanol in the feed mixture.

TABLE I

| Run Number<br>Halogen Compound | RUN NO. 1<br>$CH_2Br_2$ | | RUN NO. 2<br>HBr | | RUN NO. 3<br>$C_3F_8$ | | RUN NO. 4<br>$CH_3CH_2I$ | | RUN NO. 5<br>$BF_3$ | | RUN NO. 6<br>$CH_2Cl_2$ | |
|---|---|---|---|---|---|---|---|---|---|---|---|---|
| ppm Halogen | 0 | 10 | 0 | 10 | 0 | 500 | 0 | 4 | 0 | 50 | 0 | 50 |
| Temperatures, °C. | | | | | | | | | | | | |
| Feed Mixture, | 121 | 121 | 92 | 99 | 88 | 92 | 88 | 89 | 98 | 96 | 183 | 188 |
| Catalyst Bed, | 483 | 483 | 480 | 488 | 490 | 488 | 514 | 514 | 525 | 505 | 461 | 465 |
| Reactor Outlet | 296 | 294 | 286 | 289 | 346 | 344 | 282 | 280 | 224 | 220 | 405 | 408 |
| Pressures, Atm. | | | | | | | | | | | | |
| Reactor Inlet | 1.18 | 1.18 | 1.16 | 1.17 | 1.14 | 1.15 | 1.18 | 1.18 | 1.29 | 1.29 | 1.22 | 1.24 |
| Reactor Outlet | 1.12 | 1.12 | 1.12 | 1.12 | 1.10 | 1.12 | 1.12 | 1.12 | 1.14 | 1.14 | 1.12 | 1.12 |
| Analysis, % | | | | | | | | | | | | |
| Selectivity | 86.40 | 89.19 | 87.61 | 88.28 | 87.24 | 90.17 | 87.80 | 88.77 | 83.02 | 85.65 | 88.43 | 90.07 |
| Conversion | 61.39 | 63.02 | 64.37 | 64.26 | 65.86 | 64.17 | 62.24 | 63.06 | 59.54 | 63.85 | 63.01 | 64.48 |

The embodiments of the invention in which an exclusive privilege is claimed are defined as follows:

1. In a vapor phase process for the production of formaldehyde wherein a mixture comprising methanol and air are contacted with a silver catalyst to produce a formaldehyde-containing product, the improvement which comprises incorporating a small amount of a halogen-containing compound, in the vapor phase, into the mixture comprising methanol and air which is contacted with the said silver catalyst, the amount of said halogen-containing compound being an amount which will increase the selectivity of the reaction to formaldehyde but which will not cause loss of reaction.

2. The improvement of claim 1 wherein said halogen-containing compound is an organic halide.

3. The improvement of claim 2 wherein said organic halide is a halocarbon or halohydrocarbon, which has a boiling point at atmospheric pressure of less than about 100° C.

4. The improvement of claim 2 wherein the amount of said organic halide is such that the amount of halogen present in the mixture of methanol and air is at least 1 p.p.m. by weight based on the weight of methanol in the said mixture.

5. The improvement of claim 2 wherein the halogen substituents on said organic halide are selected from the group consisting of fluorine, chlorine, bromine, iodine and mixtures thereof.

6. The improvement of claim 2 wherein said organic halide is a saturated, acyclic halocarbon or halohydrocarbon of from 1 to 5 carbon atoms which has a boiling point of less than about 100° C.

7. The improvement of claim 6 wherein the halogen substituents on said organic halide are fluorine, and wherein the amount of said organic halide is such as to provide less than about 600 p.p.m. fluorine by weight based on the weight of methanol in said mixture.

8. The improvement of claim 7 wherein the amount of said organic halide is such as to provide from about 350 to 500 p.p.m. fluorine by weight based on the weight of methanol in said mixture.

9. The improvement of claim 6 wherein the halogen substituents on said organic halide are chlorine, and wherein the amount of said organic halide is such as to provide less than about 100 p.p.m. chlorine by weight based on the weight of methanol in said mixture.

10. The improvement of claim 9 wherein the amount of said organic halide is such as to provide from about 45 to 85 p.p.m. chlorine by weight based on the weight of methanol in said mixture.

11. The improvement of claim 6 wherein the halogen substituents on said organic halide are bromine, and wherein the amount of said organic halide is such as to provide less than about 70 p.p.m. bromine by weight based on the weight of methanol in said mixture.

12. The improvement of claim 11 wherein the amount of said organic halide is such as to provide from about 10 to 40 p.p.m. bromine by weight based on the weight of methanol in said mixture.

13. The improvement of claim 6 wherein the halogen substituents on said organic halide are iodine, and wherein the amount of said organic halide is such as to provide less than about 7 p.p.m. iodine by weight based on the weight of methanol in said mixture.

14. The improvement of claim 13 wherein the amount of said organic halide is such as to provide from about 2 to 5 p.p.m. iodine by weight based on the weight of methanol in said mixture.

15. The improvement of claim 1 wherein said halogen-containing compound is boron trifluoride, the amount of boron trifluoride utilized being such as to provide less than about 600 p.p.m. fluorine by weight based on the weight of methanol in said mixture.

16. The improvement of claim 1 wherein the amount of said boron trifluoride utilized is such as to provide from about 350 to 550 p.p.m. fluorine by weight based on the weight of methanol in said mixture.

17. In a process for the production of formaldehyde wherein a mixture comprising methanol and air in a proportion of at least 0.8 mole of air per mole of methanol is contacted in the vapor phase at a pressure of one to three atmospheres absolute with a silver catalyst maintained at a temperature of 475° to 675° C. to produce a formaldehyde-containing product, the improvement which comprises:

incorporating a small amount of a halogen-containing compound, in the vapor phase, into the mixture comprising methanol and air which is contacted with said silver catalyst, the amount of said halogen-containing compound being that which will increase the selectivity of the reaction to formaldehyde but which will not cause loss of reaction.

18. The improvement of claim 17 wherein the halogen-containing compound is a member of the group consisting of organic halides and boron trifluoride.

19. The improvement of claim 18 wherein the organic halide is a halocarbon or halohydrocarbon having a boiling point of less than about 100° C. at atmospheric pressure.

20. The improvement of claim 18 wherein the halogen-containing compound is a member of the group consisting of $CH_2Br_2$; $HBr$; $C_3F_8$; $CH_3CH_2I$; $BF_3$; and $CH_2Cl_2$.

* * * * *

REEXAMINATION CERTIFICATE (398th)

United States Patent [19]

Branecky et al.

[11] B1 4,198,351

[45] Certificate Issued Oct. 8, 1985

[54] FORMALDEHYDE PRODUCTION PROCESS

[75] Inventors: Anthony J. Branecky, Kingsville; David W. Harris, Corpus Christi, both of Tex.

[73] Assignee: Celanese Corporation, New York, N.Y.

Reexamination Request:
No. 90/000,092, Oct. 19, 1981

Reexamination Certificate for:
Patent No.: 4,198,351
Issued: Apr. 15, 1980
Appl. No.: 787,739
Filed: Apr. 15, 1977

[51] Int. Cl.[4] ............................................ C07C 45/29

[52] U.S. Cl. ................................. 568/473; 568/472; 568/471

[58] Field of Search ................. 568/473, 472, 743, 742

[56] References Cited

U.S. PATENT DOCUMENTS

| | | | |
|---|---|---|---|
| 2,643,269 | 6/1953 | Augustine | 568/473 |
| 3,928,461 | 12/1975 | Diem | 568/473 |
| 3,996,259 | 12/1976 | Lee et al. | 568/473 |
| 4,010,208 | 3/1977 | Aicher et al. | 568/473 |
| 4,098,826 | 7/1978 | Alpers et al. | 568/473 |

*Primary Examiner*—Warren B. Lone

[57] ABSTRACT

An improvement in the process for production of formaldehyde wherein a vapor phase mixture of methanol and air are passed over a silver catalyst, comprising the incorporation of a small amount of a halogen-containing compound into the mixture.

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-20 are cancelled.

* * * * *